(12) United States Patent
Berger et al.

(10) Patent No.: US 10,835,452 B2
(45) Date of Patent: Nov. 17, 2020

(54) OBTURATION COMPOSITION

(71) Applicant: DENTSPLY SIRONA Inc., York, PA (US)

(72) Inventors: Todd Patrick Berger, Owasso, OK (US); Adam Zachary Baratz, Jenks, OK (US); Sheridan Lynn Rose, Scapula, OK (US)

(73) Assignee: DENTSPLY SIRONA INC., York, PA (US)

( * ) Notice: Subject to any disclaimer, the term of this patent is extended or adjusted under 35 U.S.C. 154(b) by 30 days.

(21) Appl. No.: 15/995,714

(22) Filed: Jun. 1, 2018

(65) Prior Publication Data
US 2018/0344581 A1 Dec. 6, 2018

Related U.S. Application Data

(60) Provisional application No. 62/513,534, filed on Jun. 1, 2017.

(51) Int. Cl.

| | |
|---|---|
| A61K 6/06 | (2006.01) |
| A61K 6/851 | (2020.01) |
| C08L 5/08 | (2006.01) |
| C08L 5/06 | (2006.01) |
| C08L 5/04 | (2006.01) |
| A61K 6/17 | (2020.01) |
| A61K 6/54 | (2020.01) |
| A61K 6/56 | (2020.01) |
| A61K 6/816 | (2020.01) |
| A61K 6/818 | (2020.01) |
| A61K 6/822 | (2020.01) |
| A61K 6/887 | (2020.01) |
| A61K 6/71 | (2020.01) |

(52) U.S. Cl.
CPC ............... *A61K 6/851* (2020.01); *A61K 6/17* (2020.01); *A61K 6/54* (2020.01); *A61K 6/56* (2020.01); *A61K 6/816* (2020.01); *A61K 6/818* (2020.01); *A61K 6/822* (2020.01); *A61K 6/887* (2020.01); *C08L 5/04* (2013.01); *C08L 5/06* (2013.01); *C08L 5/08* (2013.01); *A61K 6/71* (2020.01)

(58) Field of Classification Search
CPC ................................ A61K 6/0606; A61K 6/17
See application file for complete search history.

(56) References Cited

U.S. PATENT DOCUMENTS

| | | | |
|---|---|---|---|
| 5,415,547 A | 5/1995 | Torabinejad | |
| 5,769,638 A | 6/1998 | Torabinejad | |
| 6,605,294 B2 | 8/2003 | Sawhney | |
| 7,892,342 B2 * | 2/2011 | Primus | C04B 7/02 106/35 |
| 8,658,712 B2 | 2/2014 | Primus | |
| 2015/0320645 A1 * | 11/2015 | Chow | A61C 5/50 106/35 |

FOREIGN PATENT DOCUMENTS

| | | |
|---|---|---|
| WO | 2007047994 A2 | 4/2007 |
| WO | 2011023199 A1 | 3/2011 |

OTHER PUBLICATIONS

International Search Report; PCT/US2018/035626; Sep. 6, 2018 (completed); dated Sep. 13, 2018 (mailed).
Written Opinion of the International Searching Authority; PCT/US2018/035626; Sep. 6, 2018 (completed); dated Sep. 13, 2018 (mailed).
International Preliminary Report on Patentability; PCT/US2018/035626; Sep. 6, 2018 (completed); dated Sep. 13, 2018 (mailed).

* cited by examiner

*Primary Examiner* — Michael F Pepitone
(74) *Attorney, Agent, or Firm* — Dentsply Sirona Inc.

(57) ABSTRACT

A dental composition comprising pre-reacted particulate mineral trioxide aggregate (MTA) dispersed in a hydrogel wherein the content of MTA in the composition is in the range of 20 to 50 percent by weight based on the total weight of the composition.

15 Claims, No Drawings

OBTURATION COMPOSITION

RELATED APPLICATIONS

This patent application claims the benefit of and priority to U.S. Provisional Application Ser. No. 62/513,534, filed on Jun. 1, 2017, which is herein incorporated by reference for all purposes.

FIELD OF INVENTION

The present invention relates to the field of endodontics, more particularly obturation materials for endodontics.

BACKGROUND OF THE INVENTION

The present invention relates to an endodontic obturation material. Generic obturation materials are known from the prior art, such as Dentsply Sirona's proprietary ProRoot obturation material. ProRoot is based on a reactive mineral trioxide aggregate (MTA) composition which was marketed successfully over many years in the past given inter alia the ability of the unreacted MTA to stimulate regeneration of dental tissue.

However, of existing endodontic reactive mineral trioxide aggregate (MTA) compositions requires activation by mixing with a liquid prior to application into the root canal. Given that the time-consuming mixing step cannot be avoided, the handling of the material has always been the main problem of existing endodontic reactive mineral trioxide aggregate (MTA) compositions. Moreover, given that observing optimum mixing conditions is essential for the success of the endodontic treatment, errors or variations on the part of the practitioner may be detrimental to the quality of the obturation.

Therefore, a need exists to provide an improved dental obturation material which has significantly improved handling properties while at the same time maintaining any advantages of existing endodontic reactive mineral trioxide aggregate (MTA) compositions including the ability to stimulate regeneration of dental tissue.

SUMMARY OF THE INVENTION

The present disclosure provides compositions for improving handling properties of existing endodontic reactive mineral trioxide aggregate (MTA) compositions.

In a first aspect, the present invention may provide a dental composition comprising pre-reacted particulate mineral trioxide aggregate (MTA) dispersed in a hydrogel wherein the content of MTA in the composition is in the range of 20 to 50 percent by weight based on the total weight of the composition.

In another aspect, the present invention may provide a process for the preparation of a dental composition, comprising the steps of: curing an MTA composition; milling the cured MTA to an average particle size of from 0.1 to 100 mum for obtaining a particulate cured MTA; and dispersing the particulate cured MTA in a hydrogel matrix for forming a composite composition.

In yet another aspect, any of the aspects of the present invention may be further characterized by one or any combination of the following features: wherein the particulate MTA has an average particle size of from 0.1 to 100 mum; wherein the hydrogel includes a polymeric network obtainable by polymerizing a mixture having one or more monomers selected from the group consisting of acrylic acid, acrylamide, vinyl alcohol, and combinations thereof; wherein the dental composition further comprises an organic matrix that includes sodium alginate, pectin, and/or chitosan; wherein the organic matrix is present in an amount of from 30 to 90 percent by weight based on the total weight of the composition; wherein the dental composition may be for use in endodontic treatment of a tooth; wherein the endodontic treatment is selected from indirect and direct pulp-capping, and mature and pediatric pulpotomy; wherein the endodontic treatment is the obturation of a pulp chamber; wherein the dental composition is bio inductive for cementum; wherein the dental composition stimulates a hard tissue covering areas where a blood supply exists (apical foramen, interface with healthy pulp) thereby regenerating cementum creates a biological seal; wherein the dental composition does not stimulate an inflammatory process; wherein the dental composition supports tissue regeneration; wherein the dental composition is biocompatible with pulp and periradicular tissues while not being cytotoxic in a cured or uncured state; wherein the composition is antibacterial or antimicrobial due to a pH increase; wherein the composition will produce hydroxyapatite when exposed to either blood or simulated body fluid; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise

DETAILED DESCRIPTION OF THE INVENTION

The present invention was completed based on the recognition that dental cements such as mineral trioxide aggregate's (MTA) (e.g., ProRoot MTA) ability to stimulate regeneration of dental tissue is based on the presence of calcium ions on the surface of the material. Moreover, the present invention was completed based on the further recognition that pre-reacted dental cements such as MTA may be provided as a dental composition wherein calcium ions are present on the surface of dental cements such as MTA in an amount that the ability to stimulate regeneration of dental tissue is maintained.

In one specific example, cured mineral trioxide aggregate (MTA) and/or cured dental cement particles may be provided in the present invention. Useful MTAs and/or cured dental cements are disclosed in U.S. Pat. Nos. 5,415,547, 5,769,638, 7,892,342, and 8,658,712, which are herein incorporated by reference for all purposes. Generally, a particulate material including the cement (Portland cement, alborg cement, and/or otherwise) and optionally a radiopacifier (e.g., bismuth oxide, calcium sulfate, $ZrO_2$, calcium tungstate, and/or otherwise), and optionally Hydroxyapitite is mixed with a liquid (e.g., water, SODIUM LAURYL SULFATE, POLYVINYL PYRROLIDONE, POLYVINYL ALCOHOL, PLASDONE K90, SODIUM CHLORIDE, POTASSIUM CHLORIDE, POTASSIUM DIHYDROGEN PHOSPHATE, DISODIUM PHOSPHATE, and otherwise, and mixtures thereof) and to form a dental cement composition.

Once the dental cement composition has cured (e.g., from 1 minute to 5 hours, preferably 1 minute to two hours, and more preferably from 1 minute to 30 minutes, the cured dental cement may then be reduced to particles to form cured dental cement particles ranging from 0.1 to 100 mum.

Pre-reacted or cured MTA can include the following formulations; Powders—ProRoot Gray, ProRoot White, Aalborg cement, Portland Cement, ProRoot ES or ProRoot Advanced, Aalborg cement plus zirconium oxide, Aalborg cement plus calcium tungstate, Di- & Tricalcium silicate. Liquids—Water, ProRoot Sealer Gel, ProRoot Advanced Gel, Phosphate Buffered Saline, 0.09% Saline. Any combination of the above powder/liquid works and gives unique chemical properties to the particles and will result in unique properties for the compound.

The polymeric network is obtainable by polymerizing a mixture containing one or more monomers or polymers selected from acrylic acid, acrylamide, vinyl alcohol or any other hydrogel based polymer. These polymers when mixed with water form a hydrogel and may contain from 1 to 75% water. The organic matrix is from 30 to 90 percent by weight based on the total weight of the composition. Other liquid materials may be used in the composition as provided in the Tables herein.

The compound will include additional ingredients to improve the clinical claims with the major requirement being they are compatible with an aqueous based compound. This allows for example the addition of vitamin E for anti-inflammatory claims. Another example would be the additional of a hydrophilic thickener like silica, this would manipulate the flow or handling properties. Finally, the addition of radiopacifers is not hindered so any of the biocompatible radiopacifiers is still available, calcium tungstate, tungsten, zirconium oxide, bismuth oxide, etc.

In one embodiment of a viscous or non-aqueous dental solution, the preferred viscosity enhancing agent is a polymer hydrogel. U.S. Pat. No. 6,605,294 describes that hydrogels may be formed by physical or chemical crosslinking, or a combination of these two processes. Physical crosslinking takes place as a result of ionic linkages, hydrogen bonding, Van der Waals forces, or other such physical forces. Chemical crosslinking occurs due to the formation of covalent linkages. Covalently crosslinked networks of hydrophilic polymers, including water-soluble polymers are traditionally denoted as hydrogels (or aquagels) in the hydrated state. A number of aqueous hydrogels have been used in various biomedical applications, such as, for example, soft contact lenses, wound management, and drug delivery. U.S. Pat. No. 6,605,294 is herein incorporated by reference for all purposes.

In one embodiment of a viscous or non-aqueous dental solution, the polymer hydrogel may be employed in a total amount ranging from about 0.01% to about 25.0% weight of the dental composition.

The hydrogel molecules can be polymers that release from the surface during the root canal therapy to provide a lubricating effect. The molecules can be organic or inorganic in nature. The organic molecules can hydrogel polymers, for example: polyvinyl alcohol (PVA), dimethyl acylamide (DMA), Polyvinylpyrrolidone (PVP), cellulose and cellulose derivatives, polysaccharide derivatives, Polyethylene glycol (oxide), Polyethylene glycol (oxide) derivatives and polyacrylic acids. The molecules can be small molecules, for example; surfactants, polymer additives, like slip agents and waxes.

In one specific example, the hydrogel may include the cross-linked polymer (e.g., Carbopol, a liquid component (e.g., water, propylene glycol, the like and/or otherwise and mixtures thereof), and an anti-inflammatory (e.g., tocopherol). The liquid component may be present in an amount of at least about 5%, preferably at least about 10%, and more preferably at least about 20% by wt the overall obturation composition. Furthermore, the other filler material may be present in an amount of less than about 25%, preferably less than about 20% and more preferably less than about 15% by wt the overall obturation composition. For example, the other filler material may be present in an amount ranging from about 0.1% to about 25%, preferably from about 0.5% to about 20%, and more preferably from about 1% to about 10% by wt the overall composition.

The cured dental cement particles (e.g., cured MTA particles) are suspended with in the hydrogel for incorporation into the tooth.

The present invention may include one or more fillers. Fillers having Radiopacity useful in accordance with the invention, without limitation, include inorganic fillers such as Ag, $TiO_2$, $La_2O_3$, ZrO2, $BaSO_4$, $CaWO_4$, $BaWO_4$, $Fe_2O_3$ and $Bi_2O_3$, $CeO_2$, MgO, ZnO, W, $WO_3$, lanthanide salts, polymer granulates, barium or strontium-containing glass. The glass may contain fluoride for fluoride release in vivo. When included, the radiopacifier may be present in an amount of at least about 20%, preferably at least about 30%, and more preferable at least about 40% by wt the overall composition. Furthermore, the radiopacifier may be present in an amount of less than about 80%, preferably less than about 70% and preferably less than about 60% by wt the overall obturation composition. For example, the radiopacifier may be present in an amount ranging from about 20% to about 80%, preferably from about 30% to about 70%, and more preferably from about 40% to about 60% by wt the overall composition. When included, the radiopacifier may present an include at least three radiopacifier materials. In one specific example, the at least three radiopacifiers include from about 10 to about 70% $CaWO_4$, from about 20 to about 55% $CaWO_4$ and from about 30 to about 40% $CaWO_4$.

Other fillers that may be employed include, but are not limited to silicas, aluminas, magnesias, titanias, inorganic salts, metallic oxides, (e.g., zinc oxides, silicon dioxide, calcium hydroxide, or otherwise), bioglass, mineral trioxide aggregate and glasses, though not required. Other filler material may be present in an amount of at least about 0.1%, preferably at least about 1%, and more preferably at least about 5% by wt the overall obturation composition. Furthermore, the other filler material may be present in an amount of less than about 25%, preferably less than about 20% and more preferably less than about 15% by wt the overall obturation composition. For example, the other filler material may be present in an amount ranging from about 0.1% to about 25%, preferably from about 0.5% to about 20%, and more preferably from about 1% to about 10% by wt the overall composition.

| Ingredient | Weight % |
|---|---|
| Cross-linked acrylic acid Carbopol (80 NF) | 0.05-20 |
|  | 0.75-10 |
|  | 0.5-8 |
| Radiopacifier | 10-70 |
|  | 15-55 |
|  | 25-45 |
| Cured dental cement particles (0.1 to 100 mum average particle size) | 5-65 |
|  | 10-50 |
|  | 20-40 |
| Thickener | 1-25 |
|  | 2-18 |
|  | 4-12 |
| Propylene Glycol | 0.05-10 |
|  | 0.1-7 |
|  | 0.3-4 |

-continued

| Ingredient | Weight % |
| --- | --- |
| Deionized Water | 5-65 |
|  | 10-50 |
|  | 15-35 |
| Anti-inflammatory | 0.05-10 |
|  | 0.075-7 |
|  | 0.1-3 |
| Total | 100.0 |

| Component | Chemical Name | A | B | C | D | E | F |
| --- | --- | --- | --- | --- | --- | --- | --- |
| Calcia | CaO | 30-70 | 40-60 | 50-75 | 40-65 | 30-50 | 55-75 |
| Silica | SiO2 | 10-20 | 15-30 | 15-40 | 12-30 | 5-20 | 22-38 |
| Bismuth Oxide | Bi2O3 | 5-35 | 10-30 | 0.00 | 0.00 | 25-45 | 0.00 |
| Alumina | Al2O3 | 1-5 | 1-5 | 0.5-8 | 0.5-5 | 0.5-5 | 0.5-6 |
| Sulfates | SO3 | 1-5 | 1-5 | 0.5-8 | 0.5-5 | 0.3-5 | 0.5-6 |
| Magneisa | MgO | 1-5 | 0.25-3 | 0.5-8 | 0.5-2 | 0.1-1 | 0.00 |
| Iron Oxide | Fe2O3 | 1-5 | 0.1-2 | 0.01-10 | 0.1-1 | 0.1-1 | 0.1-1 |
| Soda | Na2O | 0.05-0.5 | 0.2-2 | 0.01-1 | 0.1-1 | 0.01-1 | 0.00 |
| Potassia | K2O | 0.05-0.5 | 0.01-0.5 | 0.01-0.5 | 0.01-0.5 | 0.01-0.5 | 0.00 |
| Titania | TiO2 | 0.02 | 0.5-1 | 0.01-0.5 | 0.01-0.5 | 0.01-0.5 | 0.00 |
| Phosphorous pentoxide | P2O5 | 0.01-0.05 | 0.01-0.5 | 0.01-0.5 | 0.01-0.5 | 0-8 / 2-6 | 0.00 |
| Manganese oxide | MnO | 0.01-0.05 | 0.01-0.5 | 0.01-0.5 | 0.01-0.5 | 0.00 | 0.00 |
| Strontia | SrO | 0.01-0.05 | 0.01-0.05 | 0.01-0.5 | 0.01-0.5 | 0.01-0.5 | 0.00 |
| Zirconium Oxide | ZrO2 | 0.00 | 0.00 | 0.00 | 0-40 / 10-30 | 0.00 | 0.00 |
| Calcium Tungstate | CaWO4 | 0.00 | 0.00 | 0.00 | 0-40 / 10-30 | 0.00 | 0.00 |
| Hydroxyapatite | Ca5(PO4)3(OH) | 0.00 | 0.00 | 0.00 | 0.00 | 0-20 / 5-15 | 0.00 |
| Total |  | 100 | 100 | 100 | 100 | 100 | 100 |

| Liquid | A | B | C | D | E | F | Opt 1 | Opt 2 | Opt 3 |
| --- | --- | --- | --- | --- | --- | --- | --- | --- | --- |
| Water | 100.00 | 100.00 | 100.00 | 100.00 | 75-95 | 100.00 |  |  | 90.00 |
| Sodium lauryl sulfate | 0.00 | 0.00 | 0.00 | 0.00 | 0.00-8 / 1-6 | 0.00 |  |  |  |
| Polyvinyl alcohol | 0.00 | 0.00 | 0.00 | 0.00 | 0.00 | 0.00 |  |  |  |
| Phosphate buffered Saline |  |  |  |  |  |  | 100 |  |  |
| 0.09% Saline |  |  |  |  |  |  |  | 100 |  |
| Calcium Formate |  |  |  |  |  |  |  |  | 10 |
| Polyvinyl pyrrolidone | 0.00 | 0.00 | 0.00 | 0.00 | 5-35 / 10-30 | 0.00 |  |  |  |
| Total | 100 | 100 | 100 | 100 | 100 | 100 |  |  |  |

Workers skilled in the art will appreciate that various modifications can be made to the illustrated embodiments and description herein without departing from the spirit and scope of the present invention. It is intended that all such modifications within the spirit and scope of the present invention be covered by the appended claims.

The invention claimed is:

1. A dental composition comprising,
a pre-reacted particulate of cured mineral trioxide aggregate (MTA) and/or dental cement in an amount ranging from 20-50% by weight based on the total weight of the composition, wherein the pre-reacted particulate has an average particle size from 0.1 to 100 micrometers;
a hydrogel;
wherein the cured particulate is dispersed in the hydrogel;
wherein the hydrogel includes a polymeric network obtainable by polymerizing a mixture having one or more monomers selected from the group consisting of acrylic acid, acrylamide, vinyl alcohol, and combinations thereof.

2. A dental composition comprising:
a pre-reacted particulate of cured mineral trioxide aggregate (MTA) and/or dental cement in an amount ranging from 20-50% by weight based on the total weight of the composition, wherein the pre-reacted particulate has an average particle size from 0.1 to 100 micrometers;
a hydrogel; and
an organic matrix that includes sodium alginate, pectin, and/or chitosan;
wherein the cured particulate is dispersed in the hydrogel.

3. The dental composition according to claim 2, wherein the organic matrix is present in an amount of from 30 to 90 percent by weight based on the total weight of the composition.

4. The dental composition according to claim 1, for use in endodontic treatment of a tooth.

5. The dental composition for use according to claim 4, wherein the endodontic treatment is selected from indirect and direct pulp-capping and mature and pediatric pulpotomy.

6. The dental composition for use in the according to claim 4, wherein the endodontic treatment is the obturation of a pulp chamber.

7. The dental composition according to claim 1, wherein the dental composition:
  (i) is bio inductive for cementum,
  (ii) stimulates a hard tissue covering areas where a blood supply exists thereby regenerating cementum creates a biological seal;
  (iii) does not stimulate an inflammatory process;
  (iv) supports tissue regeneration; and/or
  (v) is biocompatible with pulp and periradicular tissues while not being cytotoxic in a cured or uncured state.

8. The dental composition according to claim 1, wherein the composition is antibacterial or antimicrobial due to a pH increase.

9. The dental composition according to claim 1, wherein the composition will produce hydroxyapatite when exposed to either blood or simulated body fluid.

10. A process for the preparation of a dental composition comprising the steps of:
  providing one or more powders selected from the group consisting of a pre-reacted particulate of cured mineral trioxide aggregate (MTA), a dental cement, a portland cement, and mixtures thereof;
  (ii) providing one or more liquids selected from the group consisting of Water, water-soluble polymer, surfactants, Phosphate Buffered Saline, 0.09% Saline, and mixtures thereof;
  (iii) mixing the one or more powders with the one or more liquids to form a cured mineral trioxide aggregate MTA and/or dental cement;
  (iv) milling, the cured MTA and/or dental cement to an average particle size of from 13.1 to 100 micrometer to form a pre-reacted particulate;
  (v) dispersing the pre-reacted particulate in a hydrogel matrix for forming a composite composition.

11. The process according to claim 10, wherein the dental composition:
  (i) is bio inductive for cementum,
  (ii) stimulates a hard tissue covering areas where a blood supply exists thereby regenerating cementum creates a biological seal;
  (iii) does not stimulate an inflammatory process;
  (iv) supports tissue regeneration; and/or
  (v) is biocompatible with pulp and periradicular tissues while not being cytotoxic in a cured or uncured state.

12. The process according to claim 11, wherein the composition is antibacterial or antimicrobial due to a pH increase.

13. The process according to claim 11, wherein the composition will produce hydroxyapatite when exposed to either blood or simulated body fluid.

14. The process of claim 10, wherein the water-soluble polymer is selected from the group consisting of polyvinyl alcohol, polyvinyl alcohol co-polymer, partially hydrolyzed polyvinyl acetates, polyvinyl-pyrrolidone, hydroxyethyl methacrylate, water-soluble poly-saccharide, polyethylene glycols, polypropylene glycols, and mixtures thereof.

15. The process of claim 10, wherein the surfactant is selected from the group consisting of alkyl sulfates, fatty acid salts with $C_{10}$-$C_{24}$ side chains, alkyl ether sulfates, alkyl sarcosinates, alkyl betaines, sarcosinates, and mixtures thereof.

* * * * *